United States Patent [19]

Chen et al.

[11] Patent Number: 4,826,430
[45] Date of Patent: May 2, 1989

[54] ADHESIVE PRIMER FOR ALUMINA BRACKETS

[75] Inventors: Albert C. Chen, East Brunswick; Robert D. DeLuca; Robin M. F. Jones, both of Pennington, all of N.J.; Donald S. Mueller, Newtown, Pa.; Mary S. Yeganeh, Willingboro, N.J.

[73] Assignee: Johnson & Johnson Consumer Products, Inc., New Brunswick, N.J.

[21] Appl. No.: 193,305

[22] Filed: May 11, 1988

Related U.S. Application Data

[60] Continuation-in-part of Ser. No. 25,438, Mar. 13, 1987, abandoned, which is a continuation-in-part of Ser. No. 806,712, Dec. 9, 1985, Pat. No. 4,681,538, which is a division of Ser. No. 602,874, Apr. 23, 1984, Pat. No. 4,595,598.

[51] Int. Cl.⁴ .............................................. A61C 3/00
[52] U.S. Cl. ........................................... 433/8; 433/9; 433/222.1; 427/2
[58] Field of Search ................... 433/8, 9, 215–228.1; 427/2

[56] References Cited

U.S. PATENT DOCUMENTS

| | | | |
|---|---|---|---|
| 2,885,366 | 5/1959 | Iler | 252/313 |
| 4,010,545 | 3/1977 | Kilian et al. | 433/9 |
| 4,180,911 | 1/1980 | Bullock | 433/228.1 X |
| 4,200,980 | 5/1980 | Johnson | 433/228.1 X |
| 4,219,617 | 8/1980 | Wallshein | 438/8 |
| 4,230,773 | 10/1980 | Bakos | 428/447 |
| 4,363,624 | 12/1982 | Johnston | |
| 4,364,731 | 12/1982 | Noiling et al. | 433/218 |
| 4,479,782 | 10/1984 | Orlowski et al. | 433/220 |
| 4,595,598 | 6/1986 | DeLuca et al. | 433/8 X |
| 4,600,390 | 7/1986 | Gobel et al. | 433/218 |
| 4,639,218 | 1/1987 | Jones et al. | 433/8 |

Primary Examiner—Nancy A. B. Swisher
Attorney, Agent, or Firm—Charles J. Metz

[57] ABSTRACT

The adhesive strength of alumina brackets to acrylic adhesive cements is enhanced by forming an essentially silica coating on the bonding surface of the bracket by the steps of coating said surface with an organosilicon compound such as a silane and then pyrolyzing the organosilicon coating to volatilize the organic components thereof to thereby leave an essentially silica coating.

6 Claims, 5 Drawing Sheets

ADHESIVE PRIMER FOR ALUMINA BRACKETS

This application is a continuation-in-part of copending application Ser. No. 25,438, filed March 13, 1987, now abandoned, which was a continuation-in-part of copending application Ser. No. 806,712, filed Dec. 9, 1985, now U.S. Pat. No. 4,681,538, which was a division of application Ser. No. 602,874, filed April 23, 1984, now U.S. Pat. No. 4,595,598.

This invention relates to the adhesive priming of alumina orthodontic brackets.

BACKGROUND OF THE INVENTION

Orthodontic brackets made of crystalline alumina (sapphire) have been proposed. Such brackets are described in U.S. patent application Ser. No. 743,851, filed on June 12, 1985 (now U.S. Pat. No. 4,639,218), assigned to the same assignee as this application.

Orthodontic brackets are usually bonded directly to teeth with an acrylic cement. It has proven to be difficult to obtain sufficient bond strength between acrylic cements and crystalline alumina brackets to ensure that such brackets will not come off during normal use.

One approach to improving the bond strength between crystalline alumina orthodontic brackets and acrylic cements is described in U.S. Pat. No. 4,595,598 and U.S. Pat. No. 4,681,538, parent applications to this application. That approach was to form a thin, adherent coating of a siliceous material such as silica on the surface of the alumina. The silica coating increases the bond strength of the alumina to acrylic cements, especially when primed with a silane coupling agent. The specific methods for forming the siliceous coating on the alumina that are disclosed in the said parent applications include cathode sputtering, plasma deposition, and electron beam evaporation.

This invention provides an improved method for forming a thin, adherent coating of a siliceous material on the surface of alumina, preferably crystalline alumina, to thereby enhance the bond strength to acrylic adhesive cements, and is particularly directed to an improved method for applying alumina orthodontic brackets to the teeth of a patient utilizing alumina brackets wherein the tooth contacting surface has a thin, adherent coating of a siliceous material produced by the method of this invention.

BRIEF SUMMARY OF THE INVENTION

The invention provides a method for applying orthodontic brackets to the teeth of a patient which comprises the steps of:

(a) providing an alumina orthodontic bracket comprising a base member including an alumina tooth contacting surface and a body member extending from said base member, said body member including walls defining an archwire groove;

(b) coating said alumina tooth contacting surface with a thin adherent coating comprising silica;

(c) applying a silane coupling agent to said alumina tooth contacting surface having thereon a thin adherent coating comprising silica; and (d) bonding said bracket to the surface of a tooth with an acrylic cement, wherein said step (b) comprises the steps of:

(e) coating said tooth contacting surface with an organosilicon compound; and (f) subjecting the product of step (e) to elevated temperature to pyrolyze the organic portion of said organosilicon compound to thereby produce an alumina orthodontic bracket having the alumina tooth contacting surface coated with a composition comprising silica.

RELEVANT ISSUED PATENTS

Norling et al. in U.S. Pat. No. 4,364,731, discloses the deposition of an oxide layer such as alumina or silica on a substrate to enhance the adhesive bonding of the substrate to polymers.

Acrylic orthodontic bracket cements are known, as is illustrated by Johnston, U.S. Pat. No. 4,363,624, and by Orlowski et al., U.S. Pat. No. 4,479,782.

A patent to Gobel et al., U.S. Pat. No. 4,600,390, discloses the deposition by flame hydrolysis of a coating of a mixture of silica and carbon to a metallic dental prosthesis as an adhesion-promoting layer. The filing date of Gobel et al., Dec. 26, 1984, is later than the Apr. 23, 1984, filing date of Applicants' parent application, Ser. No. 602,874.

Bakos, in U.S. Pat. No. 4,230,773, describes a process for reducing the surface roughness of ceramic articles, including alumina articles, by coating the surface with silicon compounds (such as silane coupling agents), drying the coated substrate, and then subjecting the substrate to elevated temperature so as to convert the silicon compounds to silicon oxides. The purpose of the Bakos invention is to produce ceramic articles that are especially suitable for the production of integrated circuits.

DETAILED DESCRIPTION OF THE INVENTION

The major novelty of the invention resides in the step of coating the bonding or tooth contacting surface of an alumina orthodontic bracket with an organosilicon compound, and then pyrolyzing the coating (in air or other oxidizing atmosphere) to volatilize the organic moieties in the coating to thereby leave a coating of a siliceus material that is predominantly silica. The organosilicon compounds that can be used for this purpose include the organosilane compounds such as those that are employed as coupling agents, silicate esters, and other organosilicon compounds. Specific illustrative examples include gamma-methacryloxypropyltrimethoxysilane, gamma-aminopropyltrimethoxysilane, vinyltriethoxysilane, allyltrimethoxylsilane, dimethyldiethoxysilane, dihydroxydiphenylsilane, triethoxysilane, trimethoxysilane, triethoxysilanol, 3-(2-aminoethylamino)propyl trimethoxysilane, gamma-glycidoxypropyltrimethoxysilane, methyltrimethoxysilane, vinyltriacetoxysilane, vinyl-tris(2-methoxyethoxy)silane, methyltriethoxysilane, tetraethyl orthosilicate, tetramethyl orthosilicate, and similar compounds.

The organosilicon compound is coated on the bonding surface by any convenient method. For instance, the alumina bracket can be (a) immersed in an organic solvent solution of the organosilicon compound, (b) removed from the solution, and (c) subjected to moderately elevated temperature to evaporate the solvent, thereby leaving a coating of the organosilicon compound on the entire surface of the bracket (including the bonding surface). Prior to the coating step, the bracket should be thoroughly cleaned and dried to enhance the adhesion of the organosilicon compound to the surface of the alumina.

After the solvent has been evaporated, the coated brackets are subjected to a pyrolysis step in an oxidizing atmosphere such as air to volatilize the organic portion of the organosilicon compound, and to leave a coating that is essentially silica on the bonding surface of the alumina bracket. The specific conditions used in the pyrolysis step are not critical; the important factors are to use a temperature high enough to volatilize (i.e., burn off) the organic moieties in the organosilicon compound, and to carry out the step for a period of time sufficient to volatilize essentially all of the organic moieties and to convert the silicon present to silica. Routine experimentation will suffice to determine the best conditions to use in particular cases.

After the coating of silica has been applied to the tooth contacting surface of the alumina bracket, the bracket is then applied to the tooth of a patient in the conventional manner by first applying a silane coupling agent to the tooth contacting surface in the known manner and then cementing the bracket to the tooth using an acrylic cement. Both silane coupling agents and acrylic cements are known in the art and may be used in the art recognized manner.

The experimental section below describes specific embodiments of the invention.

GENERAL PROCEDURES

A. Cleaning Procedure

Charge 100 mL of 45% aqueous KOH solution into a 200 mL beaker. Between 5 and 40 sapphire orthodontic brackets are added and stirred magnetically at 80° C. for 1 hour. The brackets are collected on a sieve and washed with deionized water. The brackets are collected on a sieve again and stirred in 100 mL of 3% aqueous $H_3PO_4$ (in a 200 mL beaker) at 80° C. for one hour. The brackets are collected on a sieve from the acid solution, washed in deionized water, and then stirred in 100 mL of deionized water at 80° C. for 1 hour. The brackets are finally collected on a sieve again.

B. Heating Procedure I

Sapphire brackets from the Cleaning Procedure step are heated in a furnace at 350° C. for 16 hours. They are removed and stored immediately in a desiccator containing desiccants such as "drierite".

C. Heating Procedure II

Same as above except the heating schedule is changed to 600° C. for 1 hour.

D. Sapphire Brackets

Types of sapphire test specimens have been used:

a. Brackets - Sapphire orthodontic brackets which have wire slots and tie wings on the top side and a slight curvature at the base; and b. Chips - Sapphire pieces having dimensions similar to that of brackets but have only flat surfaces on top and at the base.

Since the bond strengths of the two types are substantially equivalent, both will be referred to as "brackets".

E. Wire Mesh Substrate

Onto the flat surface of a steel cylinder having a diameter of 10 mm and a height of 20 mm is soldered a flat wire mesh (60 mesh size), which is 6 mm×6 mm in size. This substrate is used for bonding sapphire brackets. The wire mesh provides mechanical locking with the orthodontic adhesive. The substrate-sapphire assembly is then tested for bond strength on an Instron instrument.

This procedure is used to ensure that the bond strength measured is between the sapphire and the acrylic cement, and not between the cement and the steel cylinder substrate.

F. Silane Solution

Into 84 g of isopropyl alcohol in a 250-mL wide-mouth polyethylene bottle is added 2 g of gamma-methacryloxypropyltrimethoxysilane ("A-174 silane", from Union Carbide), 6 g of deionized water, and 8 g of glacial acetic acid. After closing the bottle, the contents are mixed by swirling, and the bottle is placed in a water bath at 37° C. The silane solution can be used between 2 and 23 hours after preparation.

G. Single Priming Process

Brackets which have gone through the Cleaning Procedure and Heating Procedure I (or Heating Procedure II) are removed from the desiccator and added to a beaker containing the Silane Solution (about 1-2 ml solution per bracket). After 10 minutes the brackets are collected on a sieve and transferred to an aluminum drying dish. The dish is then stored in a desiccator (no desiccant) for 30 min. The primed brackets are subsequently heated in a forced draft oven at 110° C. for 1 hour to volatilize the solvent and to cure the silane, as is conventional in the art. The brackets are then stored in a desiccator.

H. Pyrolysis Step

Brackets that have been Single Primed are heated according to Heating Procedure I or Heating Procedure II. Heating Procedure I or II (both done in air), when carried out on primed brackets, effectively pyrolyzes all the organic portion of the silane, leaving a coating that is essentially silica. The brackets having the essentially silica coating are then subjected to a second priming with a conventional silane coupling agent such as A-174 silane ("Double Priming"). The second primer layer is then used in the conventional manner as a coupling agent.

Bond Strength Testing

The two pastes of a chemical-cured orthodontic adhesive (e.g. "Achieve" marketed by Johnson & Johnson Dental Products Company or "Concise" marketed by 3M) are mixed and a small amount is applied to the base of a primed sapphire bracket, which is then pressed against the Wire Mesh Substrate for 1 min. The bonded pairs are stored in water at 37° C. for 16 hours. An Instron instrument is used to measure the shear strength of the bonds at a crosshead speed of 0.5 mm per min.

The acrylic adhesive used in these experiments was "Achieve", an acrylic cement containing bis-GMA, bisphenol A dimethacrylate, triethylene glycol dimethacrylate, and silica fillers.

The shear strength test was carried out on an Instron tester as follows:

The Wire Mesh Substrate to which is bonded the sapphire bracket is clamped securely in the Instron tester. A rod from the Instron is brought to bear against the side of the bracket at a rate of 0.5 mm per minute until the bracket breaks away from the wire mesh. The force required to break the bracket away from the wire mesh is then recorded as MPa (1 MPa=145 psi).

EXPERIMENTAL RESULTS

Example 1 - (Control)

Twelve sapphire brackets, unprimed, went through the Cleaning Procedure, Heating Procedure I, and Bond Strength Testing steps. The average shear strength obtained was 3.6 MPa (std. dev. 2.6 MPa).

Example 2 - (Control)

Twenty two sapphire brackets were treated according to the Cleaning procedure and Heating Procedure I and were then Primed with A-174 silane in the conventional manner. During the Single Priming, half of the brackets (Group A) were dried and heated (at 110° C. for 1 hour) with the bases facing up while the other half (Group B) with the bases facing down. Bond Strength Testing showed that Group A had shear strengths of 12.3 MPa (Std. dev. 7.7 MPa) and Group B had shear strengths of 16.7 MPa (Std. dev. 5.3 MPa).

Example 3 (Control)

Identical to Example 2, except the heating step (prior to priming) was changed to Heating Procedure II (600° C./1 hr). The average shear strengths were: Group A, 8.8 MPa (Std. dev. 5.1 MPa), and Group B, 17.8 MPa (Std. dev. 6.5 MPa).

Example 4

Twenty sapphire brackets went through the Cleaning Procedure and Heating Procedure I (350° C./16 hrs) steps and were then Single Primed. Double Priming was then carried out after first pyrolyzing the coating of cured silane by heating the single primed brackets at 350° C./16 hrs in air. Shear strength tests showed that Group A (bases faced uP) had bond strengths of 25.7 MPa (Std. dev. 6.9 MPa), and Group B (bases faced down) had bond strengths of 24.9 MPa (Std. dev. 11.3 MPa).

Examples 5-7

Triplicate experiments were carried out using the Heating Procedure II (600° C./1 hr) to pyrolyze the first coating of cured silane followed by Double Priming. The shear bond strengths are shown below.

|  | Group A Bases Up) | | Group B (Bases Down) | |
| --- | --- | --- | --- | --- |
|  | Ave. | Std. Dev. | Ave. | Std. Dev. |
| Example 5, MPa | 36.0 | 8.2 | 30.1 | 7.1 |
| Example 6, MPa | 29.6 | 6.9 | 31.7 | 10.6 |
| Example 7, MPa | 28.2 | 8.6 | 30.8 | 7.6 |

Example 8 - (Control)

Eighteen sapphire brackets underwent Single Priming and were then thermocycled in water between 0° C./30 sec. and 60° C./30 sec. After 700 cycles the average shear bond strength was 11.6 MPa (Std. dev. 5.8 MPa). The average bond strength after being kept in water at 37° C. for 16 hours was 18.6 MPa (Std. dev. 4.3 MPa).

Example 9

Twenty-two sapphire brackets which went through the Double Priming procedure, with Heating Procedure II (in air) between the two priming steps, were bonded to the Wire Mesh Substrates and were thermocycled between 0° C./30 sec and 60° C./30 sec. After 1,000 cycles, the average shear bond strength remained virtually unchanged at 35.7 MPa (Std. dev. 11.3 MPa).

Example 10 - (Control)

Quartz (silica) pieces having dimensions similar to those of sapphire brackets went through the Cleaning Procedure, Heating Procedure II, Single Priming, and Bond Strength Testing steps. The results are as follows: Group A (bases faced uP) 19.6 MPa (Std. dev. 9.4 MPa), and Group B (bases faced down) 21.4 MPa (Std. dev. 4.5 MPa).

Example 11-(Control-Illustrates Process of Parent Applications)

The bases of sapphire brackets were sputtered coated with silicon dioxide. Twenty four such brackets were single primed and the bond strengths determined. The results show that Group A (bases faced up) had shear strengths of 26.1 MPa (Std. dev. 9.0 MPa), and Group B (bases faced down) had shear strengths of 22.2 MPa (Std. dev. 7.5 MPa).

Example 12

Four round sapphire disks, 6 mm in diameter, and 2 mm thick, were treated as follows, in the sequence shown:

| Sample | Cleaning | Heating I | Single Priming | Heating II | Double Priming |
| --- | --- | --- | --- | --- | --- |
| 1 | Yes | Yes | No | No | No |
| 2 | Yes | Yes | Yes | No | No |
| 3 | Yes | Yes | Yes | Yes | No |
| 4 | Yes | Yes | Yes | Yes | Yes |

The samples were analyzed by ESCA (Electron Spectroscopy for Chemical Analysis) at 285 electron volts.

The results show that on the surface of the sapphire, the ratios of silicon atoms (from the primer) to aluminum atoms (from the sapphire) are as follows:

| Sample | Si/Al |
|---|---|
| 1 | 0.000 |
| 2 | 0.0460 |
| 3 | 0.1966 |
| 4 | 0.2376 |

This invention is employed in connection with alumina orthodontic brackets, preferably crystalline alumina brackets, and more preferably crystalline alpha-alumina brackets.

As used herein, the term "crystalline alumina" is intended to include only essentially monocrystalline alumina, that is, alumina comprised of a single crystal or two or more single crystals grown together longitudinally but separated by a relatively small angle (usually within 4°, determined with respect to the C-axes of neighboring single crystals) grain boundary.

In a preferred aspect of the invention, the alumina bracket is a crystalline alumina orthodontic bracket made entirely from crystalline alpha-alumina. Such a bracket can be produced by first drawing a crystalline alpha-alumina rod from a melt, wherein the rod has a predetermined cross-sectional configuration, by slicing the rod into individual blanks, and then machining the blanks to produce the bracket. As will be made apparent by the discussion below, the cross-sectional configuration of the rod is approximately the configuration of the cross-section of an orthodontic bracket taken in a plane that is perpendicular to the top and bottom faces of the bracket and is approximately parallel to the two side faces of the bracket. (By "approximately parallel" is meant not more than about 12° from parallel, for reasons that will be made clear below.) The terms "top and bottom faces" and "side faces" refer to the top, bottom, and side surfaces, respectively, of the bracket when looking directly at the front of the bracket (the "front of the bracket" is the surface opposite the tooth contacting surface) in the position the bracket would assume when installed on a tooth with the patient in the upright position. In the embodiments illustrated herein, the brackets have two pairs of tie wings, and the said plane is taken through a pair of tie wings. Thus, the said predetermined cross-sectional configuration will preferably include two pairs of tie wings and a base.

The preferred procedure for producing a crystalline alpha-alumina rod having a predetermined cross-sectional configuration is the EFG (for Edge-defined, Film-fed, Growth) modification of the Czochralski process for growing crystalline alpha-alumina. The EFG process is described by LaBelle in "EFG - The Invention and Application to Sapphire Growth", in Journal of Crystal Growth, 50, pages 8-17 (September 1980). See also LaBelle, U.S. Pat. Nos. 3,591,348, and 3,870,477, LaBelle et al., U.S. Pat. Nos. 3,701,636 and 3,915,662, and other patents and brackets cited in the Journal of Crystal Growth article.

Figure 1:
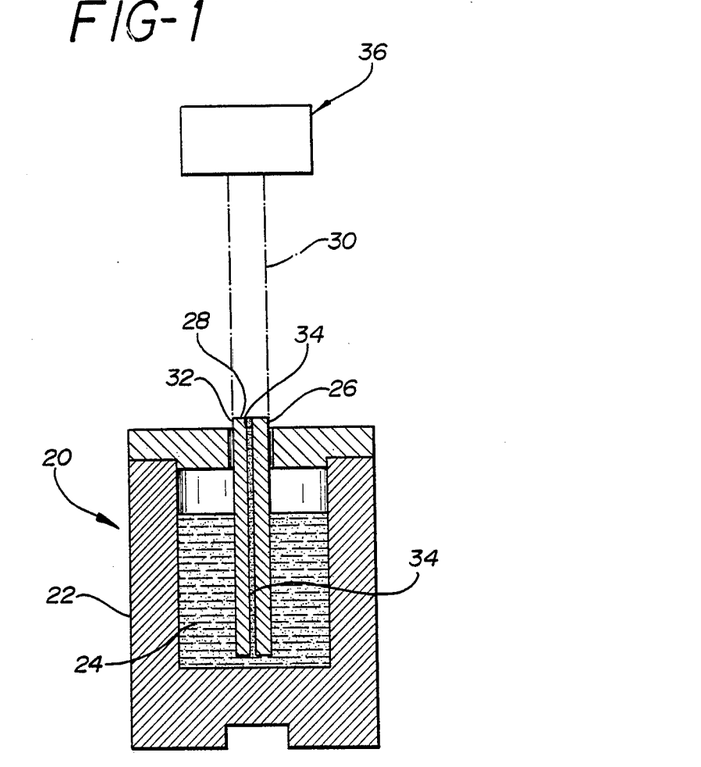
FIG. 1 is a schematic representation of apparatus for producing a crystalline alumina rod from which crystalline alumina orthodontic brackets can be machined.

FIG. 1 is a schematic representation of apparatus for producing a crystalline alpha-alumina rod having a predetermined cross-sectional configuration by the EFG process. The apparatus 20 includes a crucible 22 containing molten alumina 24. A die 26 made of a suitable material such as molybdenum or iridium is positioned such that the bottom of the die 26 is immersed in the molten alumina 24, and the top of the die 26 is above the surface of the melt 24. A vertical distance from the top of the melt 24 to the top surface 28 of the die 26 of up to 50 millimeters is permissible. (This distance is exaggerated in FIG. 1 for clarity.)

Figure 2:
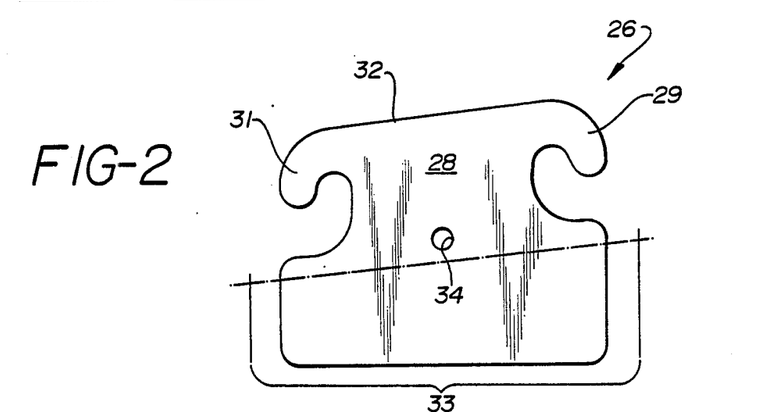
FIG. 2 is a top plan view of a die that is used in the apparatus of FIG. 1.

FIG. 2 shows the top surface 28 of the die 26. The top surface 28 is smooth, flat, and has the overall approximate shape of the desired configuration of the cross-section of the crystalline alpha-alumina rod 30 (shown in FIG. 3) from which the brackets are made, including the configuration of a pair of tie wings, shown as 29 and 31, and the base of the bracket, shown as 33. It is important that the sides 32 and the top surface 28 of the die 26 meet in a sharp 90° angle, in order to minimize imperfections in the surface of the growing rod 30. The die 26 contains a capillary passage 34 through which molten alumina 24 is drawn. The melt 24 is drawn from the crucible 22 through the capillary 34 to the top surface 28 of the die 26, where it spreads out and completely covers the said top surface 28 with a film of molten alumina. However, because molten alumina and molybdenum or iridium have the appropriate wettability relationship, the molten alumina film stops at the edge of the surface 28. Therefore, crystalline alpha-alumina crystal grown or pulled from this film of molten alumina assumes a cross-sectional configuration substantially exactly the same as the configuration of the top surface 28 of the die 26. Thus, the rod 30 (which had been started by a seed crystal, as in, the Czochralski process) pulled by a pulling mechanism 36 from the film of molten alumina on the top surface 28 of the die 26 will have a cross-sectional configuration substantially identical to the configuration of the top surface 28 of the die 26. It has been found to be convenient to grow the rod 30 to a length of about two inches (about 5 centimeters) in order to minimize any machining problems that could be caused by the failure of the rod to grow exactly straight.

The crystal orientation of the growing rod may prove to be important (at least economically, and perhaps also from a performance standpoint) in the practice of the invention. In the case of crystalline alpha-alumina, the crystal orientation can be defined with reference to the C axis of the crystal. (The C axis is perpendicular to the plane which contains the simplest arrangement of atoms in the crystal unit cell. Stated another way, the C axis is perpendicular to the plane which contains the $a_1$ and $a_2$ axes.) The minimum amount of strain developed in the growing crystal will occur if the C axis is found in a plane perpendicular to the longitudinal axis L of the rod 30. (See FIG. 3.) This has proven to be the optimum crystal orientation in some cases. (As is known in the art, the growing crystal will assume the crystal orientation of the seed crystal.) Regardless of the crystal orientation of the rod 30, it is preferred to anneal the rod 30 prior to machining so as to relieve stresses in the crystal to minimize the chances of breakage during machining. A typical annealing cycle would be to heat the rod 30 from room temperature up to 1950°-2000° C. at an even rate for about two hours, to maintain the rod 30 at 1950°-2000° C. for 4 to 6 hours, and to then cool the rod 30 down to room temperature at an even rate for two hours. The entire annealing cycle is preferably carried out under an inert atmosphere such as argon.

Figures 3, 4:
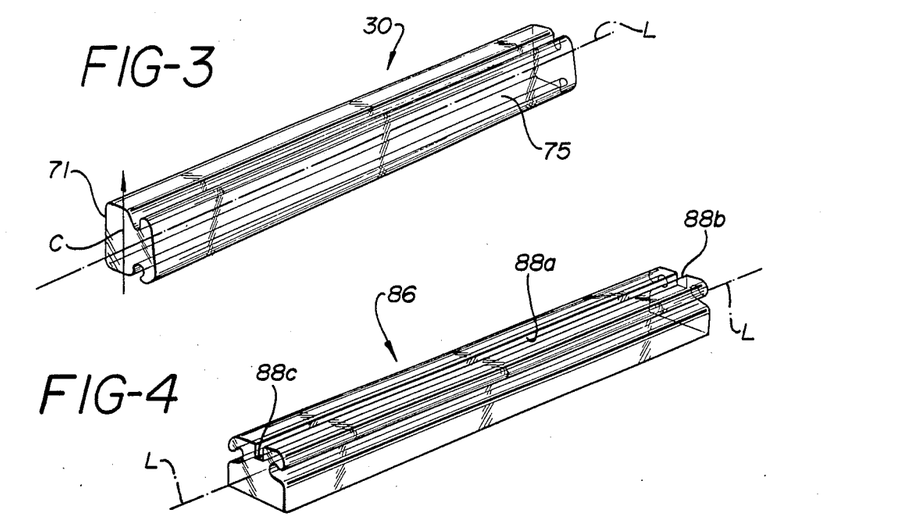
FIG. 3 is a perspective view of a crystalline alumina rod produced by the apparatus of FIG. 1.
FIG. 4 is a perspective view of the rod of FIG. 3 having an archwire groove machined therein.

The archwire groove may be ground in the rod to produce the grooved rod 86 shown in FIG. 4. (In FIGS. 4-8 and 10-11, the archwire groove is defined by walls 88a, 88b, 88c.)

Figures 5, 6:
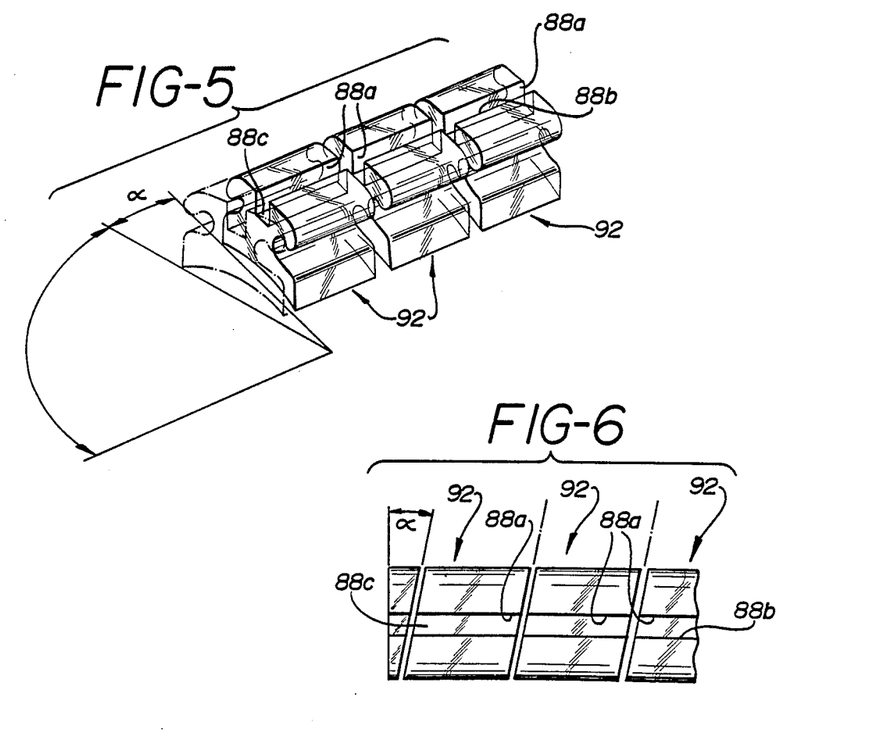
FIG. 5 is a perspective view of a series of bracket blanks cut from the rod of FIG. 4.
FIG. 6 is a top plan view of the blanks of FIG. 5.
Figure 7:
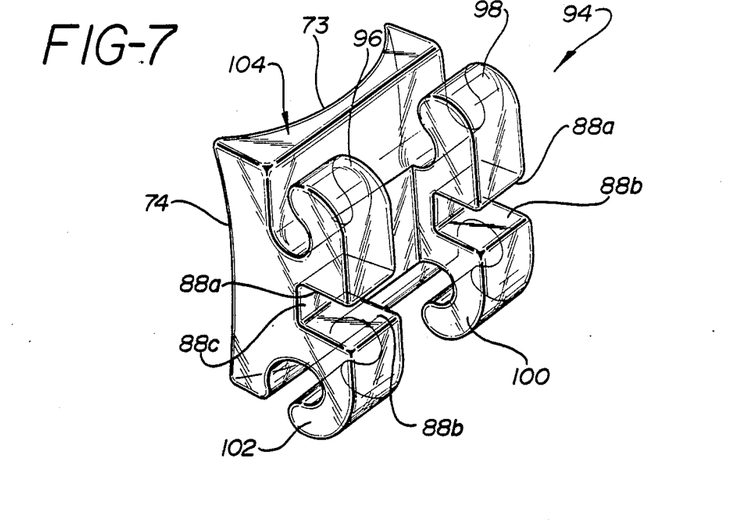
FIG. 7 is a perspective view of a crystalline alumina orthodontic bracket machined from the blanks of FIG. 6.
Figure 8:
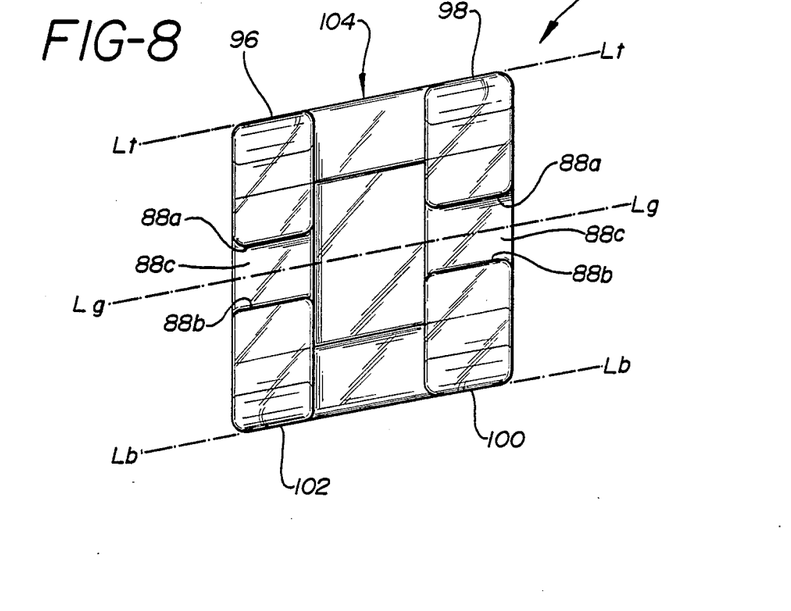
FIG. 8 is a top plan view of the bracket of FIG. 7.
Figure 9:
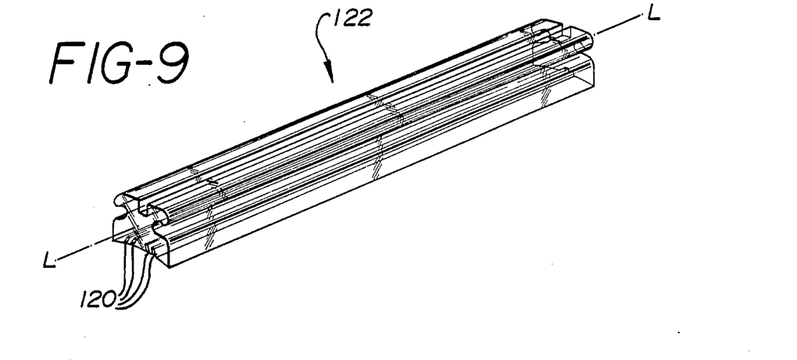
FIG. 9 is a view similar to FIG. 4, showing adhesion-promoting grooves cut in the bottom surface of the rod.

The bracket blanks 92 that are cut from the rod 86 are cut a slight angle, as is seen in FIGS. 5 and 6. Thus, instead of making the cuts in the rod 86 in a plane normal or perpendicular to the longitudinal axis L of the rod, the cuts are made in the following manner:

Holding the rod 86 in position with the longitudinal axis L in a horizontal plane and the face having the longitudinal groove on top, each cut is made in a vertical plane that is angled slightly (e.g., up to about 12°) at an angle α from the vertical plane that is perpendicular to the longitudinal axis L of the rod 86. This is best seen in FIG. 6.

Figure 10:
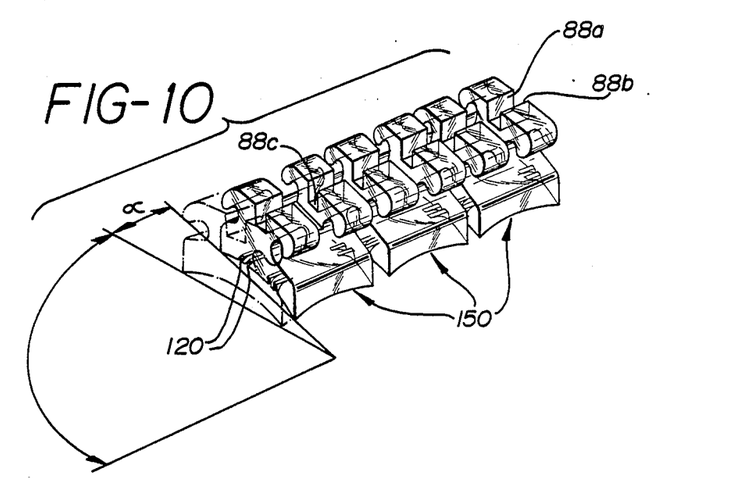
FIG. 10 is a perspective view of a series of brackets machined from the rod of FIG. 9.
Figure 11:
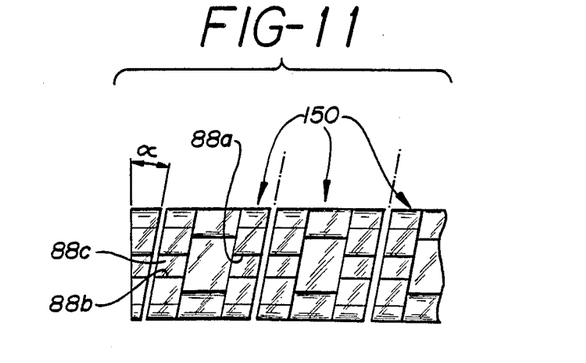
FIG. 11 is a top plan view of the brackets of FIG. 10.
Figure 12:
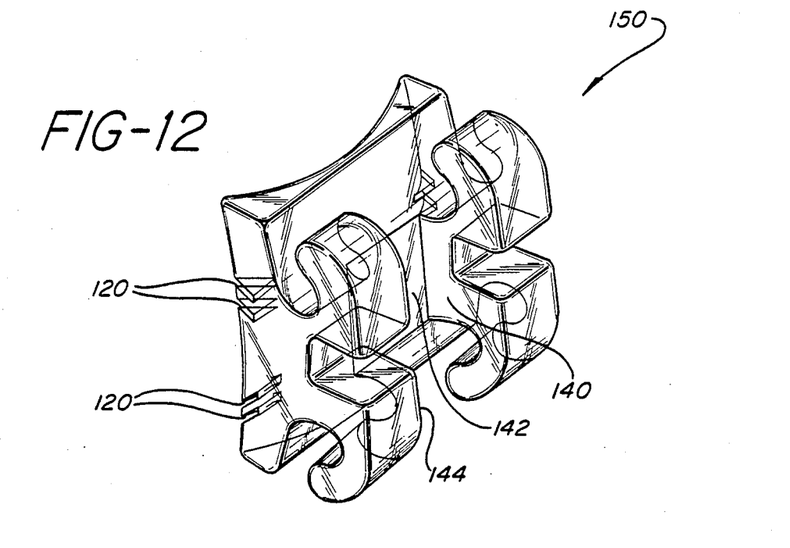
FIG. 12 is a perspective view, enlarged, of one of the brackets of FIG. 10.
Figure 13:
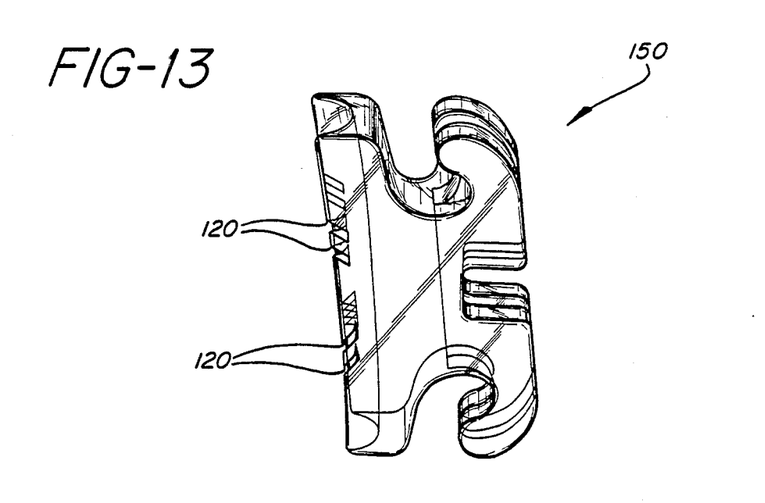
FIG. 13 is a side view of the bracket of FIG. 12.

The "saddles" (defined by walls 140, 142, 144 - see FIG. 12) and the two base concavities (shown as 73 and 74 in FIG. 7) can be machined in the bracket prior to cutting the individual brackets from the rod 86. This is preferred because it is easier to handle the rod 86 than the individual bracket blanks 92. The machining of the saddles can then be done with a diamond grinding wheel by feeding the rod stepwise to the wheel and cutting a series of grooves across the rod, wherein the said grooves will be oriented generally perpendicularly to the longitudinal axis L of the rod 86 (although, when rhomboidally shaped brackets are being produced, the cut will depart from the perpendicular by the angle α, as discussed above), and the two base concavities can be ground in a similar stepwise manner with a double-contoured diamond grinding wheel whose grinding edge is rounded or radiused to the appropriate degree so that the two concavities can be ground at the same time. FIGS. 10 and 11 show the saddles and both concavities already machined in the brackets 150 as the rod is cut into individual brackets.

After machining, the brackets are preferably annealed under the conditions disclosed above for drawn rods. Then, the brackets may be polished to smooth off contours and to remove any surface imperfections which could encourage propagation of cracks. If a polishing step is employed, a flux polishing procedure would be recommended in which the flux is partially saturated with alumina so that the removal of alumina from the surface of the bracket will proceed at a controllable rate. One preferred flux is composed of 51.2 percent $LiBO_2$, 12.8 per cent $Li_2B_4O_7$, 16 percent $Al_2O_3$, and 20 percent cent LiF (the percentages are by weight). The machined brackets are immersed in molten flux at 850° to 900° C. for a few minutes, e.g., from about four to about thirty minutes, and then removed. After cooling, the brackets can be immersed in aqueous hydrofluoric acid to remove any flux adhering to the surfaces of the brackets. Experience has demonstrated that the polishing step may be omitted, and in fact it may be undesired in many cases because of the problems it causes in holding to the dimensional specifications, especially in the archwire grooves.

Other processes for polishing the surface of crystalline alpha-alumina objects are known, and may be used if desired. Such other processes are disclosed, for example, by Noble, in U.S. Pat. No. 4,339,300, and Manasevit, in U.S. Pat. No. 3,546,036.

A means of enhancing the mechanical adhesion of the bracket to the surface of the tooth is shown in FIGS. 9-13. Small grooves 120 may be cut in the bottom surface of the rod 122, as is shown in FIG. 23. The grooves 120 extend the entire length of the rod 122. Typically, the grooves 120 will be from about 6 to 15 mils wide, with a depth about one and one-half times the width. The grooves 120 are preferably angled slightly (about 12°-15° from a direction that is generally perpendicular to the tooth contacting surface of the bracket 150, as is seen most clearly in FIG. 13). The grooves 120 will extend in a direction that is generally parallel to the orientation of the archwire groove. That is, the grooves 120 will be generally parallel to the walls 88a, 88b, 88c that define the archwire groove.

While the invention has been described most particularly in terms of bonding crystalline alumina orthodontic brackets to the surface of teeth with acrylic adhesive cements, it is applicable to the bonding of any crystalline alumina bracket to any substrate using an acrylic cement. Such other alumina brackets include ceramic polycrystalline alumina orthodontic brackets such as those described by Reynolds in U.S. Pat. Nos. 4,216,583 and 4,322,206 and Wallshein in U.S Pat. No. 4,219,617.

What is claimed is:

1. A method for applying an alumina orthodontic bracket to the tooth of a patient, said alumina orthodontic bracket comprising a base member including an alumina tooth contacting surface and a body member extending from said base member, said body member including a walls defining an archwire groove, which process comprises the steps of:
    (a) coating said alumina tooth contacting surface with a thin adherent coating comprising silica;
    (b) applying a silane coupling agent to said alumina tooth contacting surface having thereon a thin adherent coating comprising silica; and
    (c) bonding said bracket to the surface of a tooth with an acrylic cement,
    wherein said step (a) comprises the steps of:
    (d) coating said tooth contacting surface with an organosilicon compound; and
    (e) subjecting the product of step (d) to elevated temperature to pyrolyze the organic portion of said organosilicon compound to thereby produce an alumina orthodontic bracket having the alumina tooth contacting surface coated with a composition comprising silica.

2. The method of claim 1 wherein the silane is gamma-methacryloxypropyltrimethoxysilane.

3. The method of claim 2 wherein the silane is gamma-methacryloxypropyltrimethoxysilane.

4. The method of claim 1 wherein the alumina bracket is a crystalline alumina bracket.

5. The method of claim 4 wherein the organosilicon compound is a silane.

6. The method of claim 5 wherein the silane is gamma-methacryloxypropyltrimethoxysilane.

* * * * *

UNITED STATES PATENT AND TRADEMARK OFFICE
CERTIFICATE OF CORRECTION

PATENT NO. : 4,826,430

DATED : May 2, 1989

INVENTOR(S) : Albert C. Chen, Robert D. DeLuca, Robin M. F. Jones, Donald S. Mueller and Mary S. Yeganeh It is certified that error appears in the above-identified patent and that said Letters Patent is hereby corrected as shown below:

Replace claim 2 with:

-- 2. The method of claim 1 wherein the organosilicon compound is a silane. --

Signed and Sealed this

Twenty-third Day of January, 1990

*Attest:*

JEFFREY M. SAMUELS

*Attesting Officer*     *Acting Commissioner of Patents and Trademarks*